(12) United States Patent
Nakamura et al.

(10) Patent No.: US 6,197,968 B1
(45) Date of Patent: Mar. 6, 2001

(54) DECOLORIZABLE DYE

(75) Inventors: Tetsuo Nakamura; Yoshio Inagaki, both of Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/383,921

(22) Filed: Aug. 26, 1999

(30) Foreign Application Priority Data

Sep. 16, 1998 (JP) .................................. 10-261678

(51) Int. Cl.$^7$ .......................... G03C 1/22; C07D 417/00; C07D 285/14
(52) U.S. Cl. .......................... 548/152; 548/138; 548/146; 6/466
(58) Field of Search .................... 548/138, 146, 548/152; 534/605; 6/466

(56) References Cited

U.S. PATENT DOCUMENTS 3,923,524 * 12/1975 Haase ...................................... 96/140

OTHER PUBLICATIONS

Tsuchiya et al., 1987: 106:224550., Chem Abst:.*
Simov et al., J. Prakt. Chem., 1984, 326(1) pp. 151–158. Only Abs is being provided.*

* cited by examiner

Primary Examiner—Mukund J. Shah
Assistant Examiner—Pavanaram K Sripada
(74) Attorney, Agent, or Firm—Sughrue, Mion, Zinn, Macpeak & Seas, PLLC

(57) ABSTRACT

Described is a decolorizable dye represented by the following formula (I):

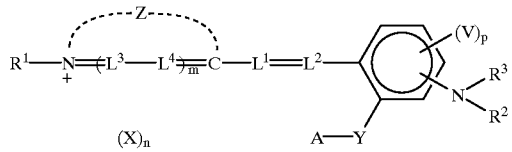

wherein $R^1$ represents an alkyl, aryl or heterocyclic group; $R^2$ and $R^3$ independently each represents a hydrogen atom or has the same meaning as $R^1$ or may be coupled together to form a ring; $L^1$ and $L^2$ independently each represents a methine group or a nitrogen atom; $L^3$ and $L^4$ independently each represents a methine group; Z represents an atomic group necessary for the formation of a 5- or 6-membered hetero ring; m stands for 0 or 1; Y represents an oxygen, sulfur, selenium or tellurium atom; A represents a hydrogen atom or a group eliminative by solution treatment; V stands for a monovalent group; p stands for 0, 1, 2 or 3, X represents a counterion, and n stands for a numeral of 0 or greater necessary for the neutralization of an electron charge in the molecule. The decolorizable dye according to the present invention retains stable color forming condition during storage but becomes colorless rightly after solution treatment.

15 Claims, No Drawings

DECOLORIZABLE DYE

BACKGROUND OF THE INVENTION

1. Field of the Invention

This invention relates to a decolorizable dye. More specifically, the present invention pertains to a decolorzable dye which becomes colorless rightly after solution treatment.

2. Description of the Related Art

Enormous efforts have been made for decreasing color remaining (residual color) which occurs after processing of a silver halide photographic material. Particularly in recent years, with a view to satisfying environmental countermeasures and user's needs, there has been a strong demand for processing speed enhancement and replenishment reduction of a photographic processing solution. A sensitizing dye or pigment (which will hereinafter be called "photographic dye" collectively) therefore needs a new molecular design utterly different from that of the conventional one.

It is widely known that color remaining of a photographic dye is effectively reduced by washing away the dye, which has hydrophilic property enhanced, into a processing solution upon photographic processing. The enhancement of hydrophilic property however usually impairs the adsorption property of a sensitizing dye to silver halide grains and adversely affects the performances of photograph such as sensitivity, fog and storage stability. It is therefore very difficult to attain reduction in color remaining and other photographic performances at the same time.

Investigations have been energetically carried out in order to remove the color of a photographic dye by making use of the chemical reaction between the dye and an additive of a photographic processing solution such as nucleophilic agent, electrophilic agent, oxidizing agent or reducing agent, or other chemical species. There are however not so many additives which do not worsen the photographic performances and complete suppression of color remaining by the reaction with a dye has been found to be difficult as a result of investigations so far made.

SUMMARY OF THE INVENTION

An object of the present invention is to provide a decolorizable dye which can stably maintain color forming conditions during storage but becomes colorless immediately after solution treatment.

As a result of extensive investigations, the object of the present invention can be attained by the following means.

(1) A decolorizable dye represented by the following formula (I):

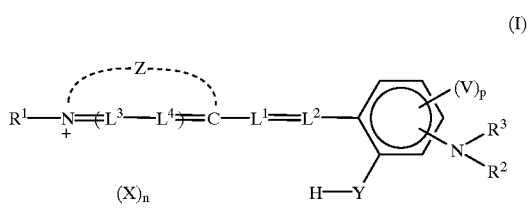

(I)

wherein $R^1$ represents an alkyl, aryl or heterocyclic group; $R^2$ and $R^3$ independently each represents a hydrogen atom, an alkyl group, an aryl group or a heterocyclic group, or may be coupled together to form a ring; $L^1$ and $L^2$ independently each represents a methine group or a nitrogen atom; $L^3$ and $L^4$ independently each represents a methine group; Z represents an atomic group necessary for the formation of a 5- or 6-membered hetero ring; m stands for 0 or 1; Y represents an oxygen, sulfur, selenium or tellurium atom; V represents a monovalent group and p stands for 0, 1, 2 or 3, and when p stands for 2 or 3, plural substituents V may be the same or different, or two of said substituents V or said substituent V and $R^2$ or $R^3$ may be coupled to form a condensed ring; X represents a counterion; and n stands for 0 or greater necessary for the neutralization of an electron charge in the molecule.

(2) A decolorizable dye represented by the following formula (II):

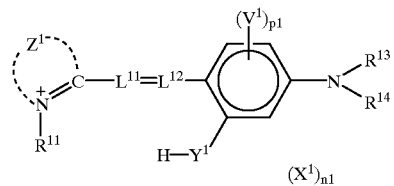

wherein $R^{11}$ represents an alkyl group; $R^{12}$ and $R^{13}$ each independently represents a hydrogen atom or an alkyl group or may be coupled together to form a ring; $L^{11}$ and $L^{12}$ each independently represents a methine group or a nitrogen atom; $Z^1$ represents an atomic group necessary for the formation of a 5- or 6-membered hetero ring; $Y^1$ represents an oxygen or sulfur atom; $V^1$ represents a halogen atom or a nitro, cyano, alkyl, aryl, alkoxy, aryloxy, alkylthio, arylthio, acyl, acyloxy, carboxy, alkoxycarbonyl, aryloxycarbonyl, carbamoyl, alkanesulfonyl, sulfo or sulfamoyl group and $p^1$ stands for 0, 1 or 2, and when $p^1$ stands for 2, two substituents $V^1$ may be the same or different, or two substituents $V^1$, or $V^1$ and $R^{12}$ or $V^1$ and $R^{13}$ may be coupled to form a condensed ring; $X^1$ represents a counterion, and $n^1$ stands for a numeral of 0 or greater necessary for the neutralization of an electron charge in the molecule.

(3) A decolorizable dye represented by the following formula (III):

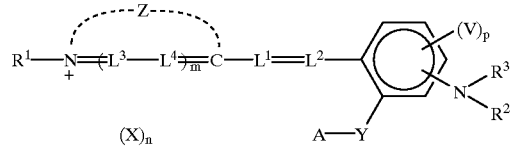

wherein $R^1_1$, $R^2$, $R^3$, $L^1$, $L^2$, $L^3$, $L^4$, Z, m, Y, V, p, X and n have the same meanings as corresponding ones in the formula (I), respectively and A represents a group eliminative by solution treatment (i.e., a group which can be eliminated by solution treatment).

(4) A decolorizable dye represented by the following formula (IV):

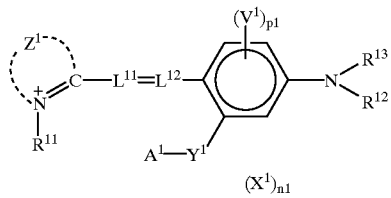

wherein $R^{11}$, $R^{12}$, $R^{13}$, $L^{11}$, $L^{12}$, $Z_1$, $V^1$, $p^1$, $X^1$ and $n^1$ have the same meanings as corresponding ones in the formula (II), respectively and $A^1$ represents an acyl, alkanesulfonyl or arenesulfonyl group From the compounds of the present invention, dye compounds which have stable color forming condition and are decolorized easily by solution treatment can be obtained.

BRIEF DESCRIPTION OF THE PREFERRED EMBODIMENTS

Compounds to be used in the present invention will next be described more specifically.

The alkyl group represented by $R^1$, $R^2$, $R^3$, $R^{11}$, $R^{12}$ or $R^{13}$ in the formula (I), (II), (III) or (IV) may be substituted or unsubstituted. In the present specification, Cn-m represents a group having n to m carbon atoms. Examples include unsubstituted $C_{1-30}$, preferably $C_{1-18}$ alkyl groups such as methyl, ethyl, propyl, isopropyl, butyl, hexyl, octyl and octadecyl; and substituted $C_{1-36}$, preferably $C_{1-24}$ alkyl groups. Examples of the substituent include carboxy group, sulfo group, cyano group, halogen atoms such as fluorine, chlorine, bromine and iodine, hydroxy group, mercapto group, $C_{1-7}$ alkoxycarbonyl groups such as methoxycarbonyl ethoxycarbonyl and benzyloxycarbonyl, $C_{6-12}$ aryloxycarbonyl groups such as phenoxycarbonyl, $C_{1-7}$ alkoxy groups such as methoxy, ethoxy and benzyloxy, $C_{6-12}$ aryloxy groups such as phenoxy and p-tolyloxy, $C_{1-7}$ acyloxy groups such as acetyloxy and propionyloxy, $C_{1-7}$ acyl groups such as acetyl, propionyl and benzoyl, carbamoyl groups such as carbamoyl, N,N-dimethylcarbamoyl, morpholinocarbonyl and piperidinocarbonyl, sulfamoyl groups such as sulfamoyl, N,N-dimethylsulfamoyl, morpholinosulfonyl and piperidinosulfonyl, $C_{6-12}$ aryl groups such as phenyl, p-chlorophenyl and p-tolyl, sulfonylcarbamoyl group and acylsulfamoyl group.

In the formula (I) or (III), the aryl group represented by $R^1$, $R^2$ or $R^3$ may be substituted or unsubstituted. Examples include unsubstituted $C_{6-30}$, preferably $C_{6-18}$ aryl groups such as phenyl, 1-naphthyl and 2-naphthyl and substituted $C_{6-36}$, preferably $C_{6-24}$ aryl groups. Examples of the substituent include those exemplified in the description of the substituted alkyl group such as carboxy group, sulfo group, cyano group, halogen atoms, hydroxy group, mercapto group, alkoxycarbonyl groups, aryloxycarbonyl groups, alkoxy groups, aryloxy groups, acyloxy groups, acyl groups, carbamoyl groups, sulfamoyl groups, aryl groups, sulfonylcarbamoyl group and acylsulfamoyl group.

In the formula (I) or (III), the heterocyclic group represented by $R^1$, $R^2$ or $R^3$ may be substituted or unsubstituted. Examples include unsubstituted $C_{1-30}$ to $C_{1-18}$ heterocyclic groups such as 2-furyl, 3-furyl, 2-thienyl, 3-thienyl, 1-pyrrolyl, 2-pyrrolyl, 3-pyrrolyl, 2-pyridyl, 3-pyridyl, 4-pyridyl, 2-pyrimidyl, 2-imidazolyl, 3-pyrazolyl, 1-piperidino, 1-morpholino and 1-indolyl; and substituted $C_{1-36}$, preferably $C_{1-24}$ heterocyclic groups. Examples of the substituent include those exemplified in the description of the substituted alkyl group such as carboxy group, sulfo group, cyano group, halogen atoms, hydroxy group, mercapto group, alkoxycarbonyl groups, aryloxycarbonyl groups, alkoxy groups, aryloxy groups, acyloxy groups, acyl groups, carbamoyl groups, sulfamoyl groups, aryl groups, sulfonylcarbamoyl group and acylsulfamoyl group.

As $R^{11}$, more preferred are unsubstituted $C_{1-8}$ alkyl groups such as methyl and ethyl, $C_{2-6}$ sulfoalkyl groups such as 3-sulfopropyl and 4-sulfobutyl, $C_{2-9}$ carboxyalkyl groups such as carboxymethyl and 4-carboxybutyl, $C_{1-8}$ mercaptoalkyl groups such as 8-mercaptooctyl, $C_{3-6}$ alkanesulfonylcarbamoylalkyl groups such as methanesulfonylcarbamoylmethyl, with unsubstituted $C_{1-4}$ alkyl groups being particularly preferred.

As $R^{12}$ or $R^{13}$, more preferred are unsubstituted $C_{1-4}$ alkyl groups such as methyl and ethyl, $C_{2-4}$ sulfoalkyl groups such as 3-sulfopropyl and 4-sulfobutyl, $C_{2-5}$ carboxyalkyl groups such as carboxymethyl and 4-carboxybutyl, $C_{1-6}$ mercaptoalkyl groups such as 6-mercaptohexyl and $C_{3-5}$ alkanesulfonylcarbamoylalkyl groups such as methanesulfonylcarbamoylmethyl. It is also preferred that $R^{12}$ and $R^{13}$ are coupled together to form a piperidine, pyrrolidine or morpholine ring. Particularly preferred as $R^{12}$ or $R^{13}$ are unsubstituted $C_{1-3}$ alkyl groups.

In the formula (I) or (III), the substitution position of the group —$NR^2R^3$ on the benzene ring is preferably the ortho or para position relative to $L^2$, with the para position being particularly preferred.

In the formula (I), (II), (III) or (IV), each of $L^1$, $L^2$, $L^{11}$ and $L^{12}$ represents a methine group or a nitrogen atom. The methine group represented by $L^1$, $L^2$, $L^{11}$ or $L^{12}$ may be substituted or unsubstituted. Preferred examples of the substituent include $C_{1-8}$ alkyl groups such as methyl, ethyl, butyl, cyclohexyl and benzyl, $C_{6-12}$ aryl groups such as phenyl, p-tolyl, p-chlorophenyl and 1-naphthyl, $C_{1-8}$ alkoxy groups such as methoxy and ethoxy, $C_{6-18}$ aryloxy groups such as phenoxy and 1-naphthyloxy, $C_{1-8}$ alkylthio groups such as methylthio and ethylthio, $C_{6-12}$ arylthio group such as phenylthio, a hydroxy group and halogen atoms such as fluorine, chlorine, bromine and iodine.

As $L^1$ or $L^{11}$, preferred is a substituted or unsubstituted methine group, with the substituted methine group being more preferred. Preferred examples of the substituent include $C_{1-4}$ alkyl groups such as methyl and ethyl, $C_{1-4}$ alkoxy groups such as methoxy and ethoxy, $C_{1-4}$ alkylthio groups such as methylthio and ethylthio, $C_{6-8}$ aryl groups such as phenyl and p-chlorophenyl, $C_{6-8}$ aryloxy groups such as phenoxy and p-chlorophenoxy and $C_{6-8}$ arylthio groups such as phenylthio and p-chlorophenylthio. As $L^2$ or $L^{12}$, preferred is an unsubstituted methine group or a nitrogen atom, with the unsubstituted methine group being more preferred. Particularly preferred as $L^1$ or $L^{11}$ is a methine group substituted by methyl, ethyl, methylthio or phenylthio group.

In the formula (I) or (III), the methine group represented by $L^3$ or $L^4$ may be substituted or unsubstituted. Substituents exemplified for $L^1$ and $L^2$ can be applied to the substituent for $L^3$ or $L^4$, but an unsubstituted methine group is preferred as $L^3$ or $L^4$.

In the formula (I) or (II), Y represents an oxygen, sulfur, selenium or tellurium atom, of which the oxygen and sulfur atoms are preferred, with the oxygen atom being particularly preferred.

In the formula (III) or (IV), $Y^1$ represents an oxygen or sulfur atom, with the oxygen atom being particularly preferred.

In the formula (I) or (III), examples of the monovalent group represented by V include halogen atoms, nitro group, cyano group, alkyl groups, aryl groups, alkoxy groups, aryloxy groups, alkylthio groups, arylthio groups, acyl groups, acyloxy groups, carboxy group, alkoxycarbonyl groups, aryloxycarbonyl groups, carbamoyl groups, alkanesulfonyl groups, sulfo group and sulfamoyl groups.

Examples of the halogen atom represented by V or $V^1$ include fluorine, chlorine, bromine and iodine atoms. As the alkyl group, unsubstituted or substituted alkyl groups such as methyl, ethyl, trifluoromethyl and methoxymethyl groups which are exemplified above as the preferred examples of the substituent $R^1$ can be mentioned as examples. Examples of the aryl group include $C_{6-12}$ aryl groups such as phenyl, p-chlorophenyl and p-tolyl, those of the alkoxy group include $C_{1-7}$ alkoxy groups such as methoxy, ethoxy and benzyloxy, those of the aryloxy group include $C_{6-12}$ aryloxy groups such as phenoxy and p-tolyloxy, those of the alkylthio group include $C_{1-7}$ alkylthio groups such as methylthio, ethylthio and benzylthio, those of the arylthio group include $C_{6-12}$ arylthio groups such as phenylthio and p-tolylthio, those of the acyl group include $C_{1-7}$ acyl groups such as acetyl, propionyl and benzoyl, those of the acyloxy group include $C_{1-7}$ acyloxy groups such as acetyloxy and propionyloxy, those of the alkoxycarbonyl group include $C_{1-7}$ alkoxycarbonyl groups such as methoxycarbonyl, ethoxycarbonyl and benzyloxycarbonyl, those of the aryloxycarbonyl group include $C_{6-12}$ aryloxycarbonyl groups such as phenoxycarbonyl, those of the carbamoyl group include $C_{1-8}$ carbamoyl groups such as carbamoyl, N,N-dimethylcarbamoyl, morpholinocarbonyl and piperidinocarbonyl, examples of the alkanesulfonyl group include $C_{1-8}$ alkanesulfonyl groups such as methanesulfonyl, and those of the sulfamoyl group include $C_{0-8}$ sulfamoyl groups such as sulfamoyl, N,N-dimethylsulfamoyl, morpholinosulfonyl and piperidinosulfonyl.

In the formula (I), (II), (III) or (IV), p or $p^1$ stands for a numeral of 2 or greater, two substituents V or $V^1$ may be coupled together to form a condensed ring. Examples of the condensed ring thus formed include benzo, naphtho, pyrido, pyrimidino, furo, pyrrolo, pyrazolo, imidazo and thieno condensed rings, with the benzo condensed ring being preferred.

It is preferred that p and $p^1$ stands for 0 or 1, with 0 being more preferred

In the formula (I), (II), (III) or (IV), examples of the 5- or 6-membered heterocyclic ring represented by Z or $Z^1$ include thiazole, benzothiazole, naphtho[1,2-d]thiazole, naphtho[2,3-d]thiazole, naphtho[2,1-d]thiazole, thiazoline, oxazole, benzoxazole, naphtho[1,2-d]oxazole, naphtho[2,3-d]oxazole, naphtho[2,1-d[]oxazole, oxazoline, selenazole, benzoselenazole, naphtho[1,2-d]selenazole, naphtho[2,3-d]selenazole, naphtho[2,1-d]selenazole, selenazoline, tellurazole, benzotellurazole, naphtho[1,2-d]tellurazole, naphtho[2,3-d]tellurazole, naphtho[2,1-d]tellurazole, tellurazoline, 3,3-dimethylindolenine, imidazole, benzimidazole, naphtho[1,2-d]imidazole, naphtho[2,3-d]imidazole, naphtho[2,1-d]imidazole, imidazoline, imidazo[4,5-b]quinoxaline, oxadiazole, thiadiazole, tetrazole, pyridine, quinoline, isoquinoline and pyrimidine rings. The heterocyclic group may have a substituent and substituents exemplified above as $V^1$ can be applied to it.

Among them, preferred are thiazole, benzothiazole, naphthothiazole, oxazole, benzoxazole, naphthoxazole, selenazole, benzoselenazole, naphthoselenazole, 3,3-dimethylindolenine, benzimidazole, naphthoimidazole and quinoline rings, of which the benzothiazole, benzoselenazole and 3,3-dimethlindolenine rings are more preferred, with the benzothiazole ring being particularly preferred.

In the formula (I), (II), (III) or (IV), X or $X^1$ is included in the formula in order to show the existence of a cation or anion when it is required for the neutralization of the electrical charge of the molecule. Whether the compound is cationic or anionic or whether it has a net ionic charge depends on its substituent. Typical examples of the cation include inorganic cations, for example, hydrogen ion, alkali metal ions such as sodium ion, potassium ion and lithium ion and alkaline earth metal ions such as calcium ion; and organic cations, for example, ammonium ions such as ammonium ion and tetraalkylammonium ion, pyridinium ion and ethylpyridinium ion. As the anion, either an inorganic anion or organic anion can be used. Examples include halide anions such as fluoride ion, chloride ion, bromide ion and iodide ion, substituted arylsulfonate ions such as p-toluenesulfonate ion and p-chlorobenzenesulfonate ion, aryldisulfonate ions such as 1,3-benzenedisulfonate ion and 2,6-naphthalenedisulfonate ion, alkylsulfate ions such as methylsulfate ion, sulfate ion, thiocyanate ion, perchlorate ion, tetrafluoroborate ion, picrate ion, acetate ion, methanesulfonate ion and trifluoromethanesulfonate ion.

Among them, preferred as the cationic ion are sodium ion, potassium ion, triethylammonium ion, tetraethylammonium ion, pyridinium ion, ethylpyridinium ion and methyl pyridinium ion, while preferred as the anionic ion include perchlorate ion, iodide ion, bromide ion and substituted arylsulfonate ions such as p-toluenesulfonate ion.

n or $n^1$ stands for a numeral of 0 or greater necessary for balancing the charge in the molecule. When an intramolecular salt is formed, it stands for 0. n or $n^1$ preferably stands for a numeral not smaller than 0 but not larger than 3.

As the compound of the formula (II), preferred is that having, in combination, 0 as $p^1$; a benzothiazole, benzoselenazole or 3,3-dimethylindolenine ring as $Z^1$; an oxygen atom as $Y^1$; a substituted methine group as $L^{11}$; an unsubstituted methine group as $L^{12}$; an unsubstituted $C_{1-4}$ alkyl group, a $C_{2-4}$ sulfoalkyl group, a $C_{2-5}$ carboxyalkyl group, a $C_{1-6}$ mercaptoalkyl group or $C_{3-5}$ alkanesulfonylcarbamoylalkyl group as $R^{12}$ or $R^{13}$; and an unsubstituted $C_{1-8}$ alkyl group $C_{2-6}$ sulfoalkyl group, $C_{2-9}$ carboxyalkyl group, $C_{1-8}$ mercaptoalkyl or $C_{3-6}$ alkanesulfonylcarbamoylalkyl group as $R^{11}$. More preferred is the above-described combination having as $Z^1$ a benzothiazole ring and as $L^{11}$ a methine group substituted any one of methyl, ethyl, methylthio and phenylthio groups.

In the formula (III), A represents a group eliminative by solution treatment and those ordinarily employed as a protective group in the synthetic organic chemistry can be used. Preferably, A is a group which is stable under neutral conditions but is eliminative under acidic or alkaline conditions. Examples of the eliminative group under acid conditions include ether type eliminative groups such as methyl, methoxymethyl, benzyl, o-nitrobenzyl, phenacyl, trimethylsilyl and t-butyldimethylsilyl, while those of the eliminative group under alkaline conditions include ester type eliminative groups such as acetyl, pivaloyl, benzoyl, levuloyl, vinyloxycarbonyl, phenylcarbamoyl, methanesulfonyl and p-toluenesulfonyl. More preferred as A are groups eliminative under alkaline conditions, of which the pivaloyl, benzoyl, levuloyl, methanesulfonyl and p-toluenesulfonyl groups.

The above-exemplified protective groups can be easily introduced, for example, in accordance with the method as described in T. W. Greene, "Protective Groups in Organic Synthesis", published by John Wiley & Sons (1981).

In the formula (IV), as $A^1$, preferred examples of the acyl group include $C_{2-10}$ acyl groups such as pivaloyl, levuloyl and benzoyl, those of the alkanesulfonyl group include $C_{1-8}$ alkanesulfonyl groups such as methanesulfonyl and those of the arylenesulfonyl group include $C_{6-20}$ arylenesulfonyl groups such as p-toluenesulfonyl.

As the compound represented by the formula (IV), preferred is the above-described preferred combination of the compound of the formula (II) further having as $A^1$ a $C_{2-10}$ acyl group, a $C_{1-8}$ alkanesulfonyl group or $C_{6-20}$ arylenesulfonyl group, of which the combination having as $A^1$ a pivaloyl, levuloyl or benzoyl group is more preferred.

The following are specific examples of the compound of the formula (I) (including the compounds of the formula (II)) according to the present invention. It should however be noted that the present invention is not limited by them.

I-1
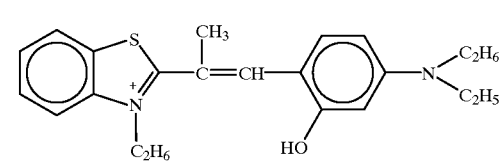
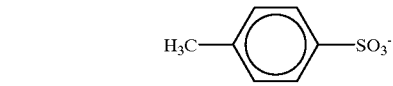

I-2
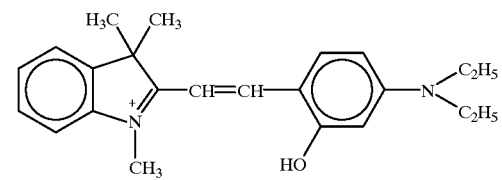

I-3
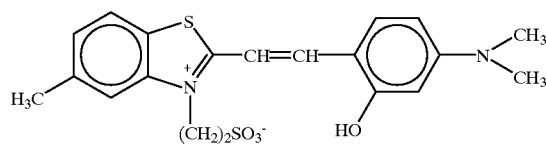

I-4
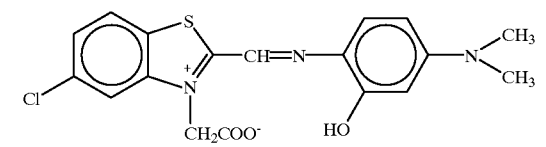

I-5
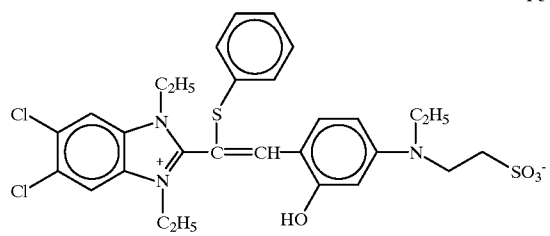

-continued

I-6
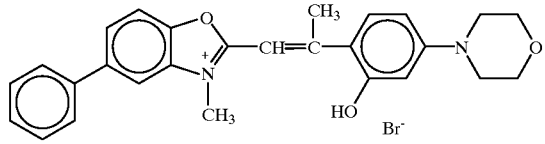

I-7
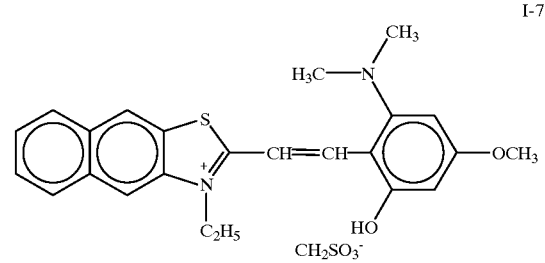

I-8
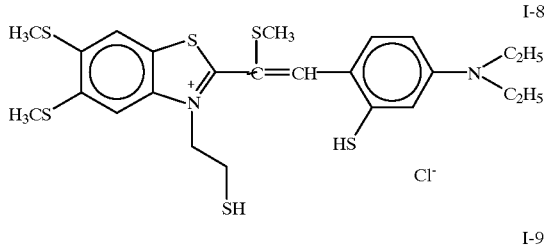

I-9
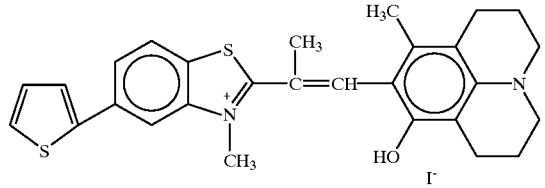

I-10
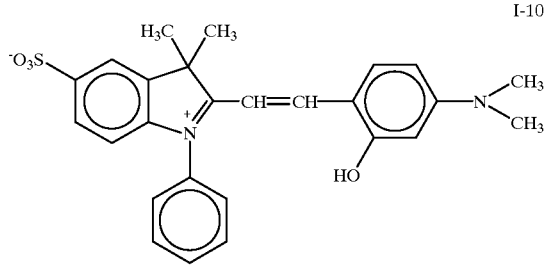

I-11
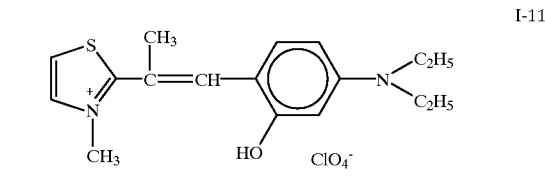

I-12

The specific examples of the compounds of the formula (III) (including the compounds of the formula (IV)) according to the present invention will next be shown. It should however be borne in mind that the present invention is not limited by them.
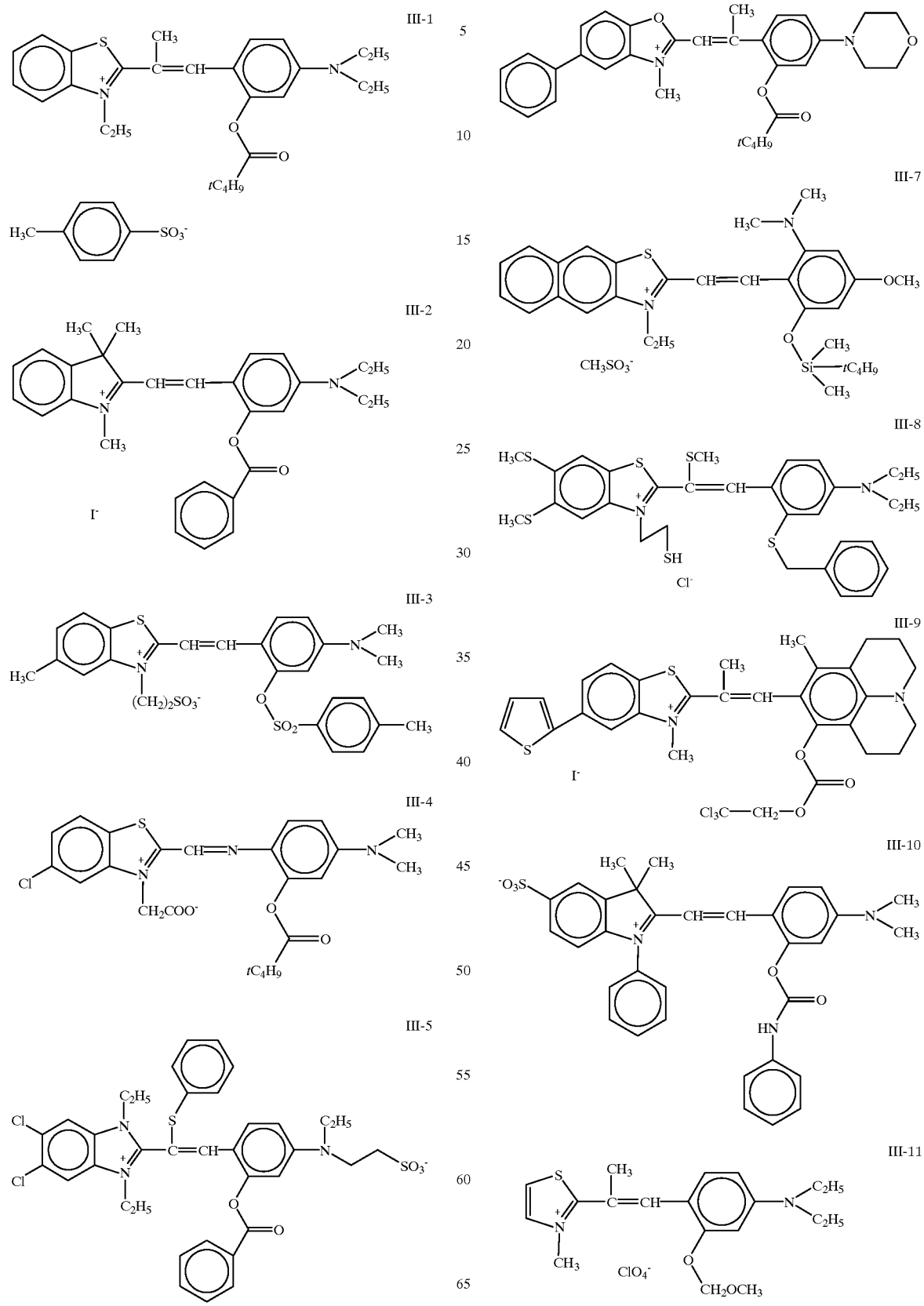

-continued

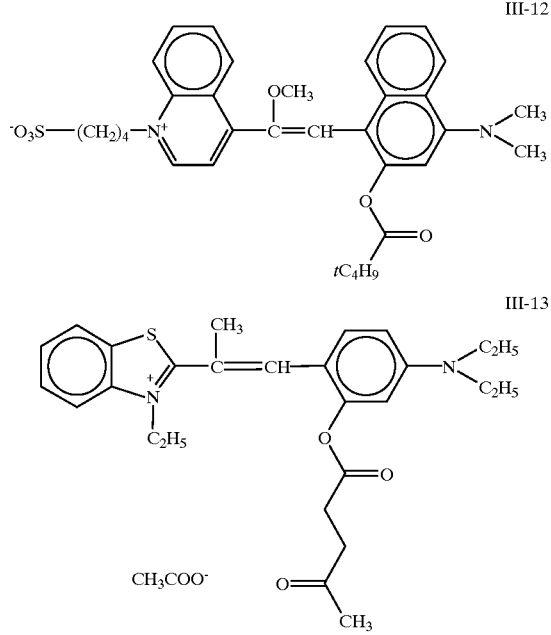

Each of the compounds represented by the formulas (I), (II), (III) and (IV) of the present invention can be synthesized in accordance with the method as described in U.S. Pat. No. 3,923,524.

EXAMPLES

The present invention will hereinafter be described more specifically by examples. It should however be borne in mind that the present invention is not limited to or by them.

Example 1
(Synthesis of Compound I-1)
(1) Synthesis of 2,3-diethylbenzothiazolium p-toluenesulfonate 2-Ethylbenzothiazole (16.3 g) and 22.0 g of ethyl p-toluenesulfonate were mixed and heated over an oil bath to 160° C. while stirring. The raw materials were once molten and after a while, a solid was precipitated. Five hours after that, heating was terminated. When the temperature was decreased to 100° C., acetone was added to disperse therein the solid. After cooling to room temperature, the solid was collected by filtration. The solid was then dried under vacuum for 2 days, whereby 31.4 g of the intended compound was obtained (yield: 86%).

(2) Synthesis of Compound I-1

In 25 ml of ethanol, 1.82 g of the compound obtained in (1) and 1.06 g of 4-diethylaminosalicylaldehyde were dissolved, followed by heating to 100° C. To the resulting solution, 0.7 ml of piperidine was added and the mixture was heated under reflux for 2 hours. Then, the solution was ice-cooled. The colorless crystals so precipitated were collected by filtration, washed with ethanol and dried under vacuum for 2 days, whereby 0.83 g of the decolorizable compound I-1 was obtained.

After the crystals were dissolved in 15 ml of methanol, 1 g of p-toluenesulfonic acid was added to the resulting solution, whereby the solution assumed reddish brown color. When the solution was concentrated by distilling off the solvent, red crystals were precipitated. The crystals were collected by filtration, washed with methanol and dried under vacuum for 2 days, whereby 0.72 g of Compound I-1 was obtained (yield: 39%). The structure of the resulting compound was confirmed by NMR, mass spectrum and elementary analysis.

Example 2
(Synthesis of Compound III-1)
(3) Synthesis of 4-diethylamino-2-pivaloyloxybenzaldehyde In 25 ml of 1,4-dioxane, 1.93 g of 4-diethylaminosalicylaldehyde was dissolved. To the resulting solution, 1.08 g of powdery sodium hydroxide and 12 mg of tetrabutylammonium hydrogensulfate were added, followed by stirring at room temperature. To the resulting heterogeneous solution, a solution of 1.45 g of pivaloyl chloride dissolved in 10 ml of 1,4-dioxane was added over 20 minutes and the mixture was stirred for 1 hour as was. To the reaction mixture, 20 ml of water was added and the mixture was extracted with ethyl acetate. The organic phase was dried over magnesium sulfate and the solvent was distilled off, whereby 2.48 g of the title compound was obtained in the form of a brown oil (yield: 89%).

(4) Synthesis of Compound III-1

In 25 ml of ethanol, 1.82 g of the compound obtained in (1) and 1.65 g of the compound obtained in (3) were dissolved, followed by heating to 100° C. To the reaction mixture, 0.7 ml of piperidine was added and the mixture was heated under reflux for 2 hours. After cooling, the solvent was distilled off and the residue was subjected to chromatography on a silica gel column. A fraction in orange color was concentrated. The concentrate was recrystallized from methanol. The resulting crystals were collected by filtration, washed with methanol and dried under vacuum for 2 days, whereby 1.52 g of Compound III-1 was obtained (yield: 67%). The structure of the resulting compound was confirmed by NMR, mass spectrum and elementary analysis.

Example 3
(Evaluation of Stability of Color Forming Condition)

A dispersion of the fine particles of Compound I-1 was prepared as described below.

In a 700-ml pot mill, 21.7 ml of water, 3 ml of a 5% aqueous solution of sodium p-octylphenoxyethoxyethanesulfonate and 0.5 g of p-octylphenoxypoly (polymerization degree: 10) oxyethylene ether were charged, followed by the addition of 1.00 g of the invention compound I-I and 500 ml of zirconium oxide beads (diameter: 1 mm) were added. The mixture was dispersed in an oscillating ball mill for 2 hours. The oscillating ball mill employed was "BO type" manufactured by Chuo Kakoki K. K. The dispersed mixture was taken out from the mill and added to 8 g of a 12.5% aqueous gelatin solution. The beads were filtered out, whereby a dispersion of the fine particles of the invention compound I-1 in gelatin was obtained.

To the dispersion, 1,2-bis(vinylsulfonylacetoamide) ethane was added as a gelatin hardener. The mixture was applied by hands onto a cellulose triacetate film support of 127 μm thick, which had been undercoated, by using a bar coater, followed by air drying overnight in a dark place at room temperature, whereby Sample 1 was prepared.

Similarly, dispersions of fine particles of the invention compounds and comparative compounds were prepared and samples 2 to 8 were each obtained by applying the dispersion to a support.

TABLE 1

| Sample | Dye | Absorption maximum | Evaluation of stability (Ex. 3) R(50° C. 80%)/ R (refrigerated) | Evaluation of discolorizability (Ex. 4) R (sample) − R (sample 9) |
|---|---|---|---|---|
| 1 (present invention) | I-1 | 500 nm | 0.90 | 0.02 |
| 2 (present invention) | I-2 | 548 nm | 0.93 | 0.05 |
| 3 (present invention) | III-2 | 523 nm | 0.99 | 0.07 |
| 4 (present invention) | III-13 | 485 nm | 0.97 | 0.04 |
| 5 (comparative example) | C-1 | 490 nm | 0.99 | 1.44 |
| 6 (comparative example) | C-2 | 495 nm | 0.34 | 0.13 |
| 7 (comparative example) | C-3 | 543 nm | 0.99 | 1.52 |
| 8 (comparative example) | C-4 | 590 nm | 0.49 | 0.22 |

C-1
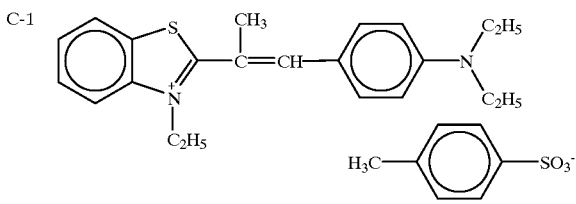

C-2
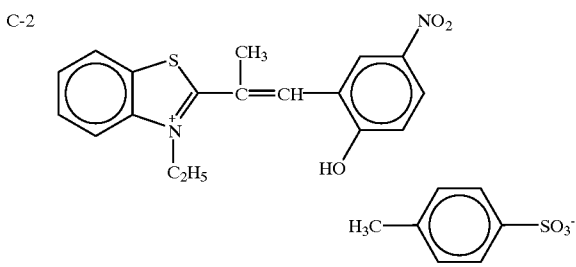

C-3
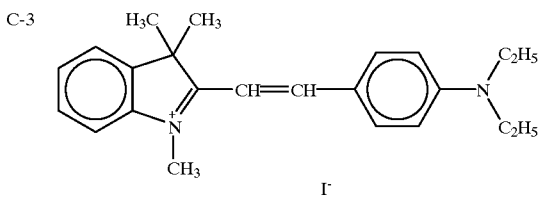

C-4
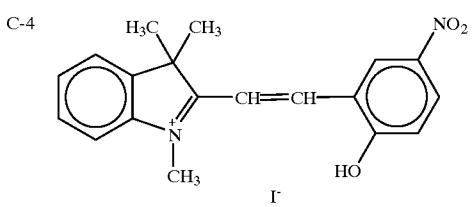

After each of the samples was refrigerated and stored under the conditions of 50° C. and 80% RH (under shading) for 3 days, its reflection spectrum was measured to determine reflectance density (R) at absorption maximum of the compound. The remaining ratio of the compound was calculated from R (50° C., 80%)/R (refrigerated). The more the ratio approaches 1, the more stable the color forming condition of the compound is. The results are shown in Table 1.

As is apparent from Table 1, it has been found that the density of the invention compound does not lower so much even when it is placed under highly humid conditions.

Example 4
(Evaluation on the Decolorizability by Solution Treatment)

In a similar manner to that described for the preparation of sample 1 in Example 3 except that Compound I-1 was not added, sample 9 was prepared. After Samples 1 to 8 prepared in Example 2 and Sample 9 were each immersed in a Britton-Robinson buffer of pH 11 for 30 minutes, the reflection spectrum was measured and reflectance density (R) at the absorption maximum of the compound was determined. The remaining amount of the compound was calculated from R (sample)−R (sample 9). The more the value approaches to 0, the better the decolorizability of the compound is.

The results are shown in Table 1.

As is apparent from Table 1, it has been found that the invention compound is easily decolorized by solution treatment and color remaining does not occur easily.

It is apparent that the use of the invention compound makes it possible to attain both stable color forming condition upon storage and decolorizability after solution treatment. Particularly, the compound of the present invention represented by the formula (II) or (V) is markedly stable in color forming condition.

What is claimed is:

1. (Amended) A decolorizable dye represented by the following formula (I):

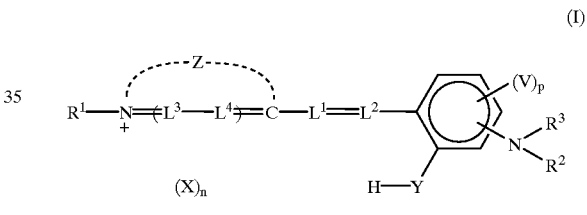

wherein $R^1$ represents an alkyl, aryl or heterocyclic group; $R^2$ and $R^3$ independently each represents a hydrogen atom, an alkyl group, an aryl group or a heterocyclic group or may be coupled together to form a ring; $L^1$ represents a substituted or unsubstituted methine group and $L^2$ represents a methine group or a nitrogen atom; $L^3$ and $L^4$ independently each represents a methine group, Z represents an atomic group necessary for the formation of a 5- or 6-membered hetero ring selected from a thiazole, benzothiazole, naphtho[1,2-d]thiazole, naphtho[2,3-d]thiazole, naphtho[2,1-d]thiazole, oxazole, benzoxazole, naphtho[1,2-d]oxazole, naphtho[2,3-d]oxazole, naphtho[2,1-d]oxazole, oxazoline, selenazole, benzoselenazole, naphtho[1,2-d]selenazole, naphtho[2,3-d]selenazole, naphtho[2,1-d]selenazole, selenazoline, tellurazole benzotellurazole, naphthor[1,2-d]tellurazole, naphtho[2,3-d]tellurazole, naphtho2,1-d]tellurazole, tellurazoline, 3,3-dimethylindolenine, imidazole, benzimidazole, naphtho[1,2-d]imidazole naphtho[2,3-d]imidazole naphtho[2,1-d]imidazole, imidazoline, imidazo[4,5-b]quinoxaline oxadiazole, thiadiazole, tetrazole, pyridine, 4-quinoline, isoquinoline and pyrimidine ring; m stands for 0 or 1; Y represents an oxygen, sulfur, selenium or tellurium atom; a substituent V represents a monovalent group and p stands for 0, 1, 2 or 3, and when p stands for 2 or 3, plural substituents V may be the same or different, or two of said substituents V or said substituent V and $R^2$ or $R^3$ may be coupled to form a condensed ring; X represents a counterion; n stands for a numeral of 0 or greater necessary for the neutralization of an electron charge in the molecule.

2. The decolorizable dye according to claim 1, which is represented by the following formula (II):

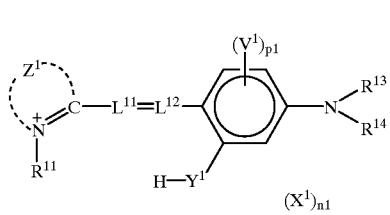

(II)

wherein $R^{11}$ represents an alkyl group; $R^{12}$ and $R^{13}$ each independently represents a hydrogen atom or a alkyl group or may be coupled together to form a ring; $L^{11}$ represents a substituted or unsubstituted methine group and $L^{12}$ represents a methine group or a nitrogen atom; $Z^1$ represents an atomic group necessary for the formation of a 5- or 6-membered heterocyclic group selected from a thiazole, benzothiazole, naphtho[1,2-d]thiazole, naphtho[2,3-d]thiazole, naphtho[2,1]-dithiazole, oxazole, benzoxazole, naphtho[1,2-dioxazole, naphtho[2,3-d]oxazole, naphtho[2, 1-d]oxazole, oxazoline, selenazole, benzoselenazole, naphtho(1,2-d]selenazole, naphtho[2,3 -d]selenazole, naphtho[2,1-d]selenazole, selenazoline, tellurazole, benzotellurazole, naphtho[1,2-d]tellurazole, naphtho[2,3-d]tellurazole, naphtho[2,1-d]tellurazole, tellurazoline, 3,3-dimethylindolenine, imidazole, benzimidazole, naphtho[1,2-d]idazole, naphtho[2,3-d]imidazole, naphtho[2,1-d]imidazole, imidazoline, imidazo[4,5-b]quinoxaline, oxadiazole, thiadiazole, tetrazole, pyridine, isoquinoline and pyrimidine ring; $Y^1$ represents an oxygen or sulfur atom; $p^1$ stands for 0, 1 or 2 and when $p^1$ stands for a ,a substituent $V^1$ represents a halogen atom or a nitro, cyano, alkyl, aryl, alkoxy, aryloxy, alkylthio, arylthio, acyl, acyloxy, carboxy, alkoxycarbonyl, aryloxycarbonyl, carbamoyl, alkanesulfonyl, sulfo or sulfamoyl group and when $p^1$ stands for 2, two substituents $V^1$ may be the same or different and each has the same meaning as defined above, or said two substituents $V^1$ or one of said substituents $V^1$ and $R^{12}$ or $R^{13}$ may be coupled to form a condensed ring; $X^1$ represents a counterion; and $n^1$ stands for a numeral of 0 or greater necessary for the neutralization of an electron charge in the molecule.

3. A decolorizable dye represented by the following formula (III):

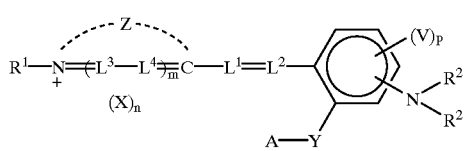

(III)

wherein $R^1$ represents an alkyl, aryl or heterocyclic group; $R^2$ and $R^3$ independently each represents a hydrogen atom, an alkyl group, an aryl group or a heterocyclic group or may be coupled together to form a ring; $L^1$ represents a substituted or unsubstituted methine group and $L^2$ represents a methine group or a nitrogen atom; $L^3$ and $L^4$ independently each represents a methine group, Z represents an atomic group necessary for the formation of a 5- or 6-membered hetero ring selected from a thiazole, benzothiazole, naphtho [1,2-d]thiazole, naphtho[2,3-d]thiazole, naphtho[2,1-d] thiazole oxazole, benzoxazole, naphthor[1,2-d]oxazole, naphtho[2,3-d]oxazole, naphtho[2,1-d]oxazole, oxazoline, selenazole, benzoselenazole, naphtho(1,2-d]selenazole, naphtho[2,3-d]selenazole, naphtho[2,1-d]selenazole, selenazoline, tellurazole, benzotellurazole, naphtho[1,2-d] tellurazole, naphtho[2,3-d]tellurazole, naphtho[2,1-d] tellurazole, tellurazoline, 3,3-dimethylindolenine, imidazole, benzimidazole, naphthor[1,2-d]imidazole, naphtho[2,3-d]imidazole, naphtho[2,1-d]imidazole, imidazoline, imidazo[4,5-b]quinoxaline, oxadiazole, thiadiazole, tetrazole, pyridine 4-quinoline, isoquinoline and pyrimidine ring; m stands for 0 or 1; Y represents an oxygen, sulfur, selenium or tellurium atom; a substituent V represents a monovalent group and p stands for 0, 1, 2 or 3, and when p stands for 2 or 3, plural substituents V may be the same or different, or two of said substituents V or said substituent V and $R^2$ or $R^3$ may be coupled to form a condensed ring; X represents a counterion; and n stands for a numeral of 0 or greater necessary for the neutralization of an electron charge in the molecule; and A represents a group eliminative by an acidic or alkaline aqueous solution treatment.

4. The decolorizable dye according to claim 3, which is represented by the following formula (IV):

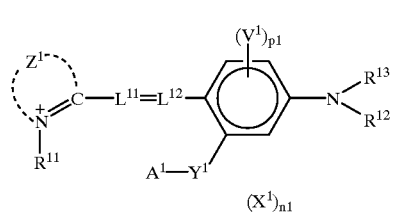

(IV)

wherein $R^{11}$ represents an alkyl group; $R^{12}$ and $R^{13}$ each independently represents a hydrogen atom or and alkyl group or may be coupled together to form a ring; $L^1$ represents a substituted or unsubstituted methine group and $L^{12}$ represents a methine group or a nitrogen atom; $Z^1$ represents an atomic group necessary for the formation of a 5- or 6-membered heterocyclic group selected from a thiazole, benzothiazole naphtho[1,2-d]thiazole, naphtho[2, 3-d]thiazole, naphtho[2,1-d]thiazole, oxazole, benzoxazole, naphtho[1,2-d]oxazole, naphtho[2,3-]ioxazole, naphtho[2,1-d]oxazole, oxazoline, selenazole, benzoselenazole, naphtho(1,2-d]selenazole, naphtho[2,3-d]selenazole, naphtho[2,1-d]selenazole, selenazoline, tellurazole, benzotellurazole, naphthor[1,2-d]tellurazole, naphtho[2,3-d]tellurazole, naphtho[2, 1-d]tellurazole, tellurazoline, 3,3-dimethylindolenine, imidazole, benzimidazole, naphtho[1,2-d]imidazole, naphtho[2,3-d]imidazole, naphtho[2,1-d]imidazole, imidazoline, imidazo[4,5-b]quinoxaline, oxadiazole, thiadiazole, tetrazole, pyridine, isoquinoline and pyrimidine ring; $Y^1$ represents an oxygen or sulfur atom; $p^1$ stands for 0, 1, or 2 and when $p^1$ stands for 1, a substituent $V^1$ represents a halogen atom or a nitro, cyano, alkyl, aryl, alkoxy, aryloxy, alkylthio, arylthio, acyl, acyloxy, carboxy, alkoxycarbonyl, aryloxycarbonyl, carbamoyl, alkanesulfonyl, sulfo or sulfamoyl group and when $p^1$ stands for 2, two substituents $V^1$ may be the same or different and each has the same meaning as defined above, or said two substituents $V^1$ or one of said substituents $V^1$ and $R^{12}$ or $R^{13}$ may be coupled to form a condensed ring; $Z^1$ represents a counterion; $n^1$ stands for a numeral of 0 or greater necessary for the neutralization of an electron charge in the molecule;

and $A^1$ represents an acyl group, alkanesulfonyl group or arenesulfonyl group.

5. The decolorizable dye according to claim 1, wherein Z represents an atomic group necessary for the formation of a 5- or 6- membered hetero ring selected from a thiazole, benzothiazole, naphthothiazole, oxazole, benzoxazole, naphthoxazole, selenazole, benzoselenazole, naphthoselenazole, 3,3-dimethylindolenine, benzimidazole, naphthoimidazole and 4-quinoline ring.

6. The decolorizable dye according to claim 1, wherein Z represents an atomic group necessary for the formation of a hetero ring selected from a benzothiazole, benzoselenazole and 3,3-dimethylindolenine ring.

7. The decolorizable dye according to claim 2, wherein $Z^1$ represents an atomic group necessary for the formation of a 5- or 6- membered hetero ring selected from a thiazole, benzothiazole, naphthothiazole, oxazole, benzoxazole, naphthoxazole, selenazole, benzoselenazole, naphthoselenazole, 3,3-dimethylindolenine, benzimidazole, naphthoimidazole and 4-quinoline ring.

8. The decolorizable dye according to claim 2, wherein $Z^1$ represents an atomic group necessary for the formation of a hetero ring selected from a benzothiazole, benzoselenazole and 3,3-dimethylindolenine ring.

9. The decolorizable dye according to claim 3, wherein Z represents an atomic group necessary for the formation of a 5- or 6- membered hetero ring selected from a thiazole, benzothiazole, naphthothiazole, oxazole, benzoxazole, naphthoxazole, selenazole, benzoselenazole, naphthoselenazole, 3,3-dimethylindolenine, benzimidazole, naphthoimidazole and 4-quinoline ring.

10. The decolorizable dye according to claim 3, wherein Z represents an atomic group necessary for the formation of a hetero ring selected from a benzothiazole, benzoselenazole and 3,3-dimethylindolenine ring.

11. A decolorizable dye according to claim 3, wherein A represents a group eliminative by an alkaline aqueous solution.

12. The decolorizable dye according to claim 4, wherein $Z^1$ represents an atomic group necessary for the formation of a 5- or 6- membered hetero ring selected from a thiazole, benzothiazole, naphthothiazole, oxazole, benzoxazole, naphthoxazole, selenazole, benzoselenazole, naphthoselenazole, 3,3-dimethylindolenine, benzimidazole, naphthoimidazole and 4-quinoline ring.

13. The decolorizable dye according to claim 4, wherein $Z^1$ represents an atomic group necessary for the formation of a hetero ring selected from a benzothiazole, benzoselenazole and 3,3-dimethylindolenine ring.

14. A decolorizable dye represented by the following formula (1):

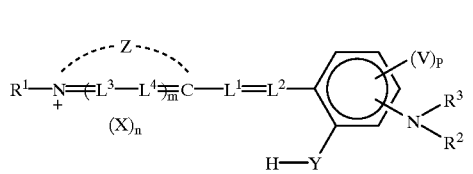

(I)

wherein $R^1$ represents an alkyl, aryl or heterocyclic group; $R^2$ and $R^3$ independently each represents a hydrogen atom, an alkyl group, an aryl group or a heterocyclic group or may be coupled together to form a ring; $L^1$ and $L^2$ each independently represent a substituted or unsubstituted methine group and represents a methine group or a nitrogen atom; $L^3$ and $L^4$ independently each represents a methine group, Z represents an atomic group necessary for the formation of a 5- or 6-membered hetero ring selected from a thiazole, naphtho[1,2-d]thiazole, naphtho[2,3-d]thiazole, naphtho[2,1-d]thiazole, oxazole, benzoxazole, naphtho[1,2-d]oxazole, naphtho[2,3-d]oxazole, naphtho[2,1-d]oxazole, oxazoline, selenazole, benzoselenazole, naphtho[1,2-d]selenazole, naphtho[2,3-d]selenazole, naphtho[2,1-d]selenazole, selenazoline, tellurazole, benzotellurazole, naphtho[1,2-d]tellurazole, naphtho[2,3-d]tellurazole, naphtho[2,1-d]tellurazole, tellurazoline, 3,3-dimethylindolenine, imidazole, benzimidazole, naphtho[1,2-d]imidazole, naphtho[2,3-d]imidazole, naphtho[2,1-d]imidazole, imidazoline, imidazo[4,5-b]quinoxaline, oxadiazole, thiadiazole, tetrazole, pyridine, 4-quinoline, isoquinoline and pyrimidine ring; m stands for 0 or 1; Y represents an oxygen, sulfur, selenium or tellurium atom; a substituent V represents a monovalent group and p stands for 0, 1, 2 or 3, and when p stands for 2 or 3, plural substituents V may be the same or different, or two of said substituents V or said substituent V and $R^2$ or $R^3$ may be coupled to form a condensed ring; X represents a counterion; n stands for a numeral of 0 or greater necessary for the neutralization of an electron charge in the molecule.

15. A decolorizable dye represented by the following formula (III):

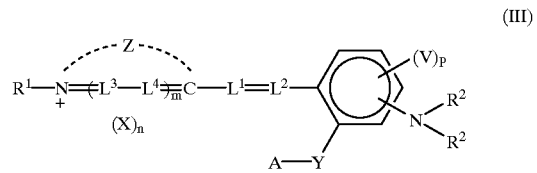

(III)

wherein $R^1$ represents an alkyl, aryl or heterocyclic group; $R^2$ and $R^3$ independently each represents a hydrogen atom, an alkyl group, an aryl group or a heterocyclic group or may be coupled together to form a ring; $L^1$ and $L^2$ each independently represent a substituted or unsubstituted methine group and represents a methine group or a nitrogen atom; $L^3$ and $L^4$ independently each represents a methine group, Z represents an atomic group necessary for the formation of a 5- or 6-membered hetero ring selected from a thiazole, naphtho[1,2-d]thiazole, naphtho[2,3-d]thiazole, naphtho[2,1-d]thiazole, oxazole, benzoxazole, naphtho[1,2-d]oxazole, naphtho[2,3-d]oxazole, naphtho[2,1-d]oxazole, oxazoline, selenazole, benzoselenazole, naphtho[1,2-d]selenazole, naphtho[2,3-d]selenazole, naphtho[2,1-d]selenazole, selenazoline, tellurazole, benzotellurazole, naphtho[1,2-d]tellurazole, naphtho[2, 3-d]tellurazole, naphtho[2,1-d]tellurazole, tellurazoline, 3,3-dimethylindolenine, imidazole, benzimidazole, naphtho[1,2-d]imidazole, naphtho[2,3-d]imidazole, naphtho[2,1-d]imidazole, imidazoline, imidazo[4,5-b]quinoxaline, oxadiazole, thiadiazole, tetrazole, pyridine, 4-quinoline, isoquinoline and pyrimidine ring; m stands for 0 or 1; Y represents an oxygen, sulfur, selenium or tellurium atom; a substituent V represents a monovalent group and p stands for 0, 1, 2 or 3, and when p stands for 2 or 3, plural substituents V may be the same or different, or two of said substituents V or said substituent V and $R^2$ or $R^3$ may be coupled to form a condensed ring; X represents a counterion; and n stands for a numeral of 0 or greater necessary for the neutralization of an electron charge in the molecule; and A represents a group eliminative by an acidic or alkaline aqueous solution treatment.

* * * * *